(12) United States Patent
Daaka et al.

(10) Patent No.: US 7,531,164 B2
(45) Date of Patent: May 12, 2009

(54) PREVENTING BACTERIAL OR VIRAL INFECTIVITY AND COMPOSITION CONTAINING INFECTION PREVENTING ADDITIVE

(75) Inventors: Yehia Daaka, Chapel Hill, NC (US); Jonathan S. Stamler, Chapel Hill, NC (US)

(73) Assignee: Duke University, Durham, NC (US)

( * ) Notice: Subject to any disclaimer, the term of this patent is extended or adjusted under 35 U.S.C. 154(b) by 507 days.

(21) Appl. No.: 11/544,559

(22) Filed: Oct. 10, 2006

(65) Prior Publication Data

US 2007/0092512 A1 Apr. 26, 2007

Related U.S. Application Data

(60) Provisional application No. 60/728,750, filed on Oct. 21, 2005.

(51) Int. Cl.
*A61K 49/00* (2006.01)
*A61K 47/00* (2006.01)
*A61K 33/00* (2006.01)

(52) U.S. Cl. .............. 424/9.1; 424/9.2; 424/278.1; 424/718

(58) Field of Classification Search ............ 424/9.1, 424/9.2, 278.1, 718
See application file for complete search history.

(56) References Cited

OTHER PUBLICATIONS

Wang, G., et al., "Nitric Oxide Regulates Endocytosis by S-Nitrosylation of Dynamin", Proceedings of the National Academy of Sciences of the United States of America, vol. 103, No. 5, Jan. 31, 2006; pp. 1295-1300.

*Primary Examiner*—Rodney P. Swartz
(74) *Attorney, Agent, or Firm*—Bacon & Thomas, PLLC

(57) ABSTRACT

A nitric oxide synthesis inhibitor or nitric oxide scavenger is administered to prevent development of infection, to prevent development of a cancer where overstimulation of a receptor contributes to the cancer development, and to prevent loss of beta agonist responsivity and as a treatment in combination with a receptor blocker. Compositions include nitric oxide synthesis inhibitor or nitric oxide scavenger containing spermicidal compositions, nasal steroid compositions, urinary tract infection prophylaxis compositions, compositions for prophylaxis of EGFR associated cancer and human blood component(s) composition for transfusion.

14 Claims, No Drawings

PREVENTING BACTERIAL OR VIRAL INFECTIVITY AND COMPOSITION CONTAINING INFECTION PREVENTING ADDITIVE

CROSS-REFERENCE TO RELATED APPLICATION

This application claims the benefit of U.S. Provisional Application No. 60/728,750, filed Oct. 21, 2005, the whole of which is incorporated herein by reference.

TECHNICAL FIELD

This invention is directed to prophylaxis against bacterial and/or viral infection and development of cancer and compositions containing additive for such prophylaxis. In some cases these compositions provide risk of infection without said additive. This invention is also directed at preventing loss of beta agonist responsivity in the cases of heart failure and asthma. The invention is also directed at potentiating receptor blocking therapy.

BACKGROUND OF THE INVENTION

It has been previously considered that nitric oxide production in the body provides defense against bacterial and viral infection and inhibits proliferation of pathologically proliferating cells including pathologic bacteria and pathologic viruses and pathologically proliferating cancer cells and that nitric oxide synthesis inhibitors and nitric oxide scavengers are therefore generally contraindicated in the case of infections and cancer.

SUMMARY OF THE INVENTION

It is known that internalization of receptors (including those of bacteria and viruses and those associated with development of cancer and of desensitization) is necessary to maintain the function of these receptors. It is known that endogenously produced dynamin mediates the internalization of bacteria and viruses and various receptors including G-protein coupled receptors, e.g., beta-receptors, and including EGFR receptors (e.g., tyrosine kinase), into endocytotic machinery for internalization of the receptors and in particular that dynamin clips off a vesicle to allow entrance into a cell. It follows that interference with this function of dynamin, will prevent the commencement and development of infection and diseases associated with overstimulation of receptors and effects related to the desensitization of receptors.

It has been discovered herein that nitric oxide plays a crucial role in the receptor internalization causing function of dynamin. In particular, it has been discovered herein that dynamin contains a critical cysteine residue which when S-nitrosylated activates dynamin to potentiate uptake of bacteria, viruses and receptors. It has been discovered herein that mutants of dynamin without this critical cysteine do not have this uptake potentiating function and that interference with the S-nitrosylation inhibits or blocks this function.

Background Example 1 hereinafter is directed to showing that nitric oxide regulates endocytosis by S-nitrosylation of dynamin at a single cysteine residue (C607) and that a mutant protein bearing a C607A substitution does not increase its endocytotic activity in response to nitric oxide and that expression of the C607A substituted dynamin and nitric oxide synthase inhibition inhibit both receptor internalization and bacterial invasion.

Background Example 2 hereinafter shows inhibition of dynamin function on HIV endocytotic uptake by a nitric oxide synthase inhibitor.

The discovery here explains why many disease states are characterized by "nitric oxide deficiency," i.e., the nitric oxide has been depleted to maintain the function of receptors and internalization machinery.

However, the discovery is applicable only to prophylaxis against development of disease and the start or spread (first few days) thereof. After an infection develops it is important for nitric oxide to be present to kill bacteria and viruses as part of an immune response.

One embodiment herein, denoted the first embodiment, is directed to a method of prophylaxis against bacterial and/or viral infection in a mammal at risk for development of a bacterial or a viral infection, said method comprising administering to said mammal an infection development preventing or infection mitigating effective amount (or a dynamin activation preventing or inhibiting effective amount) of a nitric oxide synthesis inhibitor or a nitric oxide scavenger and discontinuing said administration within one month or within two days after infection is observed or determined in the mammal, whichever is shorter. The nitric oxide synthesis inhibitor or nitric oxide scavenger can be used in combination with other prophylactic or treatment therapy, e.g., administration of antibacterial agent or antiviral agent, e.g., Tamiflu®.

Another embodiment herein denoted the second embodiment, in a first aspect, is directed to a method of prophylaxis of development in a mammal at risk for development of a cancer where overstimulation of receptor, e.g., EGFR, contributes to development of the cancer, comprising administering to said mammal an EGFR (or other receptor) internalization preventing or inhibiting effective amount of a nitric oxide synthesis inhibitor or a nitric oxide scavenger and discontinuing administration within a month or within two days after said cancer is observed or determined in the mammal, whichever is shorter. The nitric oxide synthesis inhibitor or nitric oxide scavenger can be used in combination with other prophylactic anticancer therapy.

The second embodiment in a second aspect, is directed to a method of prophylaxis against heart attack in a mammal with plaque accumulation comprising administering an amount of anti-VEGFR antibody effective to prevent destabilization of plaque and a VEGFR internalization preventing or inhibiting (dyamin activation preventing or inhibiting) effective amount of a nitric oxide synthesis inhibitor or a nitric oxide scavenger, and discontinuing administration of the nitric oxide synthesis inhibitor or nitric oxide scavenger within a month and if a heart attack occurs.

Still another embodiment herein, denoted the third embodiment, is directed to a method of preventing loss of beta agonist responsivity in a heart failure patient with normal blood pressure with compensated heart failure or in an asthma patient with normal tone (less than 12% decrease in basal FEV1 (relative to patient's baseline)), comprising administering to the heart failure patient or administering to the asthma patient between exacerbations a beta agonist desensitization preventing effective amount of a nitric oxide synthesis inhibitor or nitric oxide scavenger, the administration being discontinued when there is uncompensated illness or an exacerbation or when the patient is admitted to the hospital.

Still another embodiment herein, denoted the fourth embodiment, is directed to a spermicidal composition comprising a spermicidally effective amount of a spermicide and an infection preventing or mitigating effective amount of an NO synthesis inhibitor or an NO scavenger.

Still another embodiment herein, denoted the fifth embodiment, is directed to a nasal composition for topical application for the prevention of development of infection and/or mitigation of the symptoms thereof, comprising a nasal congestion preventing or mitigating effective amount of a nasal steroid and an infection development preventing or infection mitigating effective amount of an NO synthesis inhibitor or an NO scavenger.

Still another embodiment herein, denoted the sixth embodiment, is directed to a urinary tract infection prophylaxis composition comprising an infection development preventing or infection mitigating effective amount of a non-antibiotic NO synthesis inhibitor (otherwise administration of tetracyclines for urinary tract infection treatment anticipates) or an NO scavenger and an antimicrobial effective amount of an antimicrobial when the patient is at risk for microbial infection and/or antifungal effective amount of an antifungal when the patient is at risk for fungal infection.

Yet another embodiment herein, denoted the seventh embodiment, is directed to a composition for prophylaxis of development of EGFR associated cancer in those at risk therefor, comprising an anti EGFR blocking effective amount of anti-EGFR antibody and an EGFR internalization blocking effective amount of an NO synthesis inhibitor or an NO scavenger.

Yet another embodiment herein, denoted the eighth embodiment, is directed to a human blood component(s) composition for transfusion into a human in need thereof comprising whole blood, red blood cells, plasma, hemoglobin based blood substitute, albumin, platelets, and/or white blood cells containing as an additive an infection development preventing or infection mitigating amount of an NO synthesis inhibitor or an NO scavenger.

Yet another embodiment herein denoted the ninth embodiment, is directed to a method of treating a mammal affected with a disorder treated by receptor blocking therapy comprising administering a receptor blocking effective amount of receptor blocker and a said receptor internalization preventing or inhibiting (or a dynamin activation preventing or inhibiting) effective amount of a nitric oxide synthesis inhibitor or a nitric oxide scavenger.

The term "infection mitigating" as used herein means that when an infection develops, it is milder than without the prophylaxis.

DETAILED DESCRIPTION

Nitric oxide (NO) synthesis inhibitors for all embodiments herein, unless otherwise indicated, are the same and include arginine antagonists, citrulline antagonists, antibiotic nitric oxide synthesis inhibitors, L-aspartate antagonists, argininosuccinate synthetase induction blocking agents, NOS mRNA expression inhibitors including antibiotics that have this function, and tetrahydrobiopterin synthesis induction or utilization blocking agents.

The arginine antagonists include inhibitors of nitric oxide formation from arginine and include inhibitors of synthesis of nitric oxide catalyzed by eNOS or nNOS and inhibition of synthesis of nitric oxide catalyzed by iNOS as demonstrated, for example, in vitro and in vivo in any of the tests carried out in U.S. Pat. No. 5,028,627. The citrulline antagonists and L-aspratate antagonists and argininosuccinate synthetase induction blocking agents are effective because they prevent formation of arginine from citrulline and L-aspartate and can be determined by testing as described in U.S. Pat. No. 5,545,625. Antibiotic inhibitors can be used in the first, second, third, fourth, fifth, seventh, eighth and ninth embodiments.

Antibiotic inhibitors are excluded from use in the sixth embodiment herein because tetracyclines which are iNOS inhibitors and therefore inhibitors of nitric oxide synthesis, have been used to treat urinary tract infections. The tetrahydrobiopterin synthesis induction or utilization blockers are effective because tetrahydrobiopterin is a cofactor in the induction of nitric oxide synthesis; these are described and are determined as described in U.S. Pat. Nos. 5,877,176 and 5,874,433. As used herein, the term "antibiotic" means an agent that directly blocks development of infection by killing bacteria.

The arginine antagonists include arginine derivatives that inhibit the formation of nitric oxide from arginine catalyzed by any nitric oxide synthase; these include $N^G$-substituted arginines and $N^G,N^G$-disubstituted arginines which are active in the L-configuration; these include NG-alkyl arginines where the alkyl is methyl, ethyl, propyl or butyl (the methyl analog in the L-configuration is referred to as L-NMA or L-NMMA), $N^G$-nitro-L-arginine methyl ester (commonly referred to as L-NAME), and aminoarginine. The $N^G,N^G$-disubstituted arginines include asymmetric dimethyl-L-arginine (commonly referred to as ADMA). The arginine antagonists also include $N^6$-(hydrazinoiminomethyl) lysine as described in U.S. Pat. No. 5,132,453; and compounds including $N^{67}$-substituted ornithine moieties or $N^\epsilon$-substituted lysine moieties or monalkyl carbon substituted $N^\delta$ substituted omithine or $N^\epsilon$ substituted lysine moieties including L-thiocitrulline and L-homothiocitrulline and $N^\delta$-(2-thienyl)methylimino-L-ornithine as described in U.S. Pat. No. 5,424,447; and guanidine substituted arginines or homoarginines based on monalkyl carbon-substituted ornithines or lysines including RS-β-methyl-$N^\omega$-methyl-DL arginine and RS-γ-methyl-$N^\omega$-methyl-DL arginine as described in U.S. Pat. No. 5,281,627; and nitric oxide synthesis inhibitors described in U.S. Pat. No. 5,364,881 including S-methyl-L-thiocitrulline and S-methyl-L-homothiocitrulline; and arginase as described in U.S. Pat. No. 5,196,195.

Citrulline antagonists are described in U.S. Pat. No. 5,545,625 and include L-thiocitrulline, L-homothiocitrulline, and $N^\omega$-alkyl-L-citrulline wherein the alkyl contains 1 to 6 carbon atoms including $N^\omega$-methyl-L-arginine.

The antibiotic nitric oxide synthesis inhibitors include, for example, minocycline and tetracycline.

L-aspartate antagonists are described in U.S. Pat. No. 5,545,625 and include D-aspartate.

Argininosuccinate synthetase induction blocking agents are described in U.S. Pat. No. 5,545,625 and include antibiotics that bind to the upstream regulatory region of the aminosuccinate synthetase gene and include mithramycin, chromomycins and olinomycins.

The NOS mRNA expression inhibitors include tetracyclines including tetracycline, and doxycycline and minocycline as described in Amin, A.R., et al., Proc. Natl. Acad. Sci. USA 93(24), 14014-14019 (Nov. 26, 1996), as well as siRNA.

The blockers of induction of tetrahydrobiopterin synthesis and/or utilization include guanosine triphosphate cyclohydrolase I inhibitors including substituted pyrimidines, oxidized pterins and reduced pterins that are not substrates for the pterin salvage pathway, e.g., 2,4-diamino-6-hydroxypyridine (DAHP) and N-acetylserotonin as described in U.S. Pat. No. 5,877,176; and substituted 4-phenyl (hydropyridines), tetrahydropterin analogs that do not replace tetrahydrobiopterin as a substrate for nitric oxide synthase, including (6R,S)-6,7-dimethyl-tetrahydrobiopterin and (6R,S)-tetrahydrofolic acid and 2,4-diamino, 4,6-diamino and 2,5-diamino mono- and disubstituted pyrimidines and the corresponding pyrimidine-3-oxides as described in U.S. Pat. No. 5,874,433.

Nitric oxide (NO) scavengers for all embodiments herein, are the same Nitric oxide scavenging activity is readily assessed by using sodium nitroprusside or a NONOate as a nitric oxide donor in vivo and determining the regulatory (NO reduction) effect of additive of a potential NO scavenger with analysis by Greiss reagent, e.g., as described in Baliga, MS., et al., Nahrung 47(4), 261-4 (August, 2003) and Jagetia, et al., Journal of Medicinal Food 7(3), 343-348 (September, 2004). As defined in Wikipedia a NONOate is a compound having the formula $R^1R^2N(-NO-)-N+O$.

Nitric oxide scavengers for use herein include Vitamin B12 (hydroxocobalamin), cyanocobalamin, hemoglobin, flavohemoglobin, heme, myoglobin, phenyl-4,4,5,5-tetramethylimidazoline-1-oxyl-3-oxide (PTIO), 2-(4-carboxyphenyl)-4,4,5, 5-tetramethylimidazoline-1-oxyl-3-oxide (cPTIO or carboxy-PTIO), ruthenium (III) polyaminocarboxylate complex, and dithiocarbamates which chelate iron to form complex which irreversibly binds free NO including pyrrolidine dithiocarbamate, NOX-100, NOX-200 and NOX-700.

A preferred nitric oxide synthesis inhibitor for use in all the embodiments herein is L-methylarginine (called LNMA or LNMMA). A preferred nitric oxide scavenger for use in all the embodiments herein is vitamin B12.

We turn now to the first embodiment herein. Viruses, the uptake of which into endocytotic machinery is mediated by dynamin and which cause viral infections referred to in the recitation of the first embodiment, include cold viruses, flu viruses, bird flu viruses, HIV viruses, stomatitis virus, T-cell lymphoma viruses, adenoviruses including adeno associated virus type 2, hepatitis viruses; coxsackie virus B3, Ebola virus, Echovirus 1 (EV1), rotaviruses, rhinovirus type 2, human rhinovirus 14 (HRV14), simian virus 40 (SV40), hantaan virus, canine parvovirus, Semliki Forest virus (SFV), and Sindbis virus.

Pathogenic bacteria, the uptake of which into endocytotic machinery is mediated by dynamin and causing bacterial infections referred to in recitation of the first embodiment are pathogenic "E.coli" including "E.coli" 0157:H7.

Those at risk for infections referred to in the first embodiment include those having sexual intercourse, especially those having unprotected sexual intercourse, those expected to undergo or who have had whole blood, red blood cell or plasma transfusions, those who are or are expected to be immunocompromised, e.g., from AIDS or on immune suppressing drugs, those in schools during a cold or other pandemic, premature babies, babies at risk for rhinovirus infection, anyone during a risk period for flu or bird flu, those with a history of urinary tract infection, those eating undercooked ground beef, raw milk or unpasteurized cider that may contain pathogenic "E.coli", food from infected or contaminated food handler, e.g., from changing a diaper or not washing hands, and anyone swimming in water contaminated with sewage.

The amount of nitric oxide synthesis inhibitor or nitric oxide scavenger administered is an infection development preventing or infection mitigating amount (or a dynamin activation preventing or inhibiting amount). Dosage for a particular nitric oxide synthesis inhibitor or nitric oxide scavenger for a particular at risk status can be established by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure. In general, dosage ranges from nanomolar to millimolar blood concentration in vivo Dosage for LNMA ranges, for example, from 1 µM to 20 µM (0.1-20 gms/day) and for vitamin B-12 ranges, for example, from 2-20 mg/day.

Administration can be topical, oral or IV and the kind of administration may be related to at risk status. For example, before sexual intercourse, the dynamin activation preventing or inhibiting agent can be administered topically in a spermicidal gel or vaginal cream or other spermicidal composition or spermicide administering device. After sexual intercourse, said agent can be administered orally. In respect to a blood product transfusion, said agent is preferably included in the product transfused. For babies or school children or during a pandemic or flu or bird flu outbreak, said agent can be administered topically, e.g., to nasal passages or to nasal mucosa, or orally. For those with a history of urinary tract infection or those who are or are expected to be immunocompromised, said agent can be administered orally.

The duration of administration should be no more than a month so that nitric oxide is available as part of an immune response and should be discontinued within two days after an infection is noted or determined so nitric oxide is available as an immune response to internalized bacteria or virus.

The administration stems viral and bacterial replication and downstream consequences, e.g., illness or death in the case of HIV AIDS, development of flu or bird flu in the case of flu or bird flu virus, development of urinary tract infection, and development of sepsis or gastroenteritis in the case of pathogenic "E. coli".

For flu the administration of the first embodiment is preferably used as a preventative in association with yearly immunization with flu vaccine.

For flu or bird flu the administration of the first embodiment used in the preventative treatment is preferably associated with administration of Tamiflu® (oseltamivir phosphate) if symptoms appear or can be used in association with Tamiflu® where the Tamiflu® is administered as a preventative. Amantadine and/or rimantadine can be administered in conventional dosages in association with the nitric oxide synthesis inhibitors in the first embodiment as a preventative for influenza A; and zanamivir can be administered in conventional dosage in association with the nitric oxide synthesis in the first embodiment as a preventative for influenza A and influenza B. If flu symptoms appear, aspirin 600 mg or acetaminophen 650 mg PO q 4 h, may be administered for adults, and for children, acetaminophen 10 to 15 mg/kg q 4 to 6 hr not to exceed 5 doses/24 hrs may be administered. Nasal decongestant can be administered (e.g., oxymetazoline, 1-3 drops or sprays per nostril) topically to relieve nasal obstruction.

We turn now to the first aspect of the second embodiment herein which is directed at prophylaxis of development of a cancer associated with overstimulation of a receptor, e.g., EGFR, VEGFR, and ABL, FLT, PDGFR, FGFR, cKIT and SYK receptors.

Cancers associated with overstimulation of EGFR include, for example, human solid tumor cancers including lung (non small cell lung), breast, prostate, colon, ovary and head and neck cancers; pancreatic cancers; brain and myelogenous leukemia. These kinds of cancers are described in Krause, D. S., et al., New England Journal of Medicine 353(2), 172-187 (Jul. 14, 2005), which is incorporated herein by reference.

Cancers associated with overstimulation of VEGFR include, for example, colon, ovary cancer, breast cancer, gastric cancer and small cell lung cancer. These kinds of cancer are described in Krause, D. S., et al., New England Journal of Medicine 353(2), 172-187 (Feb. 14, 2005).

Cancers associated with overstimulation of ABL receptor include, for example, chronic myelogenous leukemia and adult lymphoblastic leukemia.

Cancers associated with overstimulation of FLT receptor include, for example, laryngeal cancer and pancreatic cancer.

Cancers associated with overstimulation of PDGFR include, for example, breast cancer and ovarian cancer.

Cancers associated with overstimulation of FGF receptor include, for example, multiple myeloma.

Cancers associated with overstimulation of cKIT receptor include, for example, small cell lung cancer and gastrointernal stomach cancer.

Cancers associated with overstimulation of SYK receptor include, for example, myelodysplastic syndrome.

Those at risk for development of these cancers are those who are immunocompromised or expected to become immunocompromised, e.g., from AIDS or immune suppressing drugs, those having previously had or who have a family history of these kinds of cancers, and those having genetic predisposition.

The amount of a nitric oxide synthesis inhibitor or nitric oxide scavenger administered for the first aspect second embodiment is an EGFR (or other cancer associated receptor) internalization inhibiting amount or a dynamin activation preventing or inhibiting amount. Dosage for a particular nitric oxide synthesis inhibitor or nitric oxide scavenger for a particular receptor associated cancer and at risk status can be established by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure or (f) by assessing effect or receptor production. In general, dosage ranges from nanomolar to millimolar blood concentration in vivo. Dosage for LNMA ranges, for example, from 1 μM to 20 mM blood concentration (1.1-20 gms/day) and dosage for vitamin B-12 ranges, for example, from 2-20 mg/day.

Administration for the first aspect of the second embodiment can be oral or IV.

The duration of administration for the second embodiment should be no more than one month so that nitric oxide is available for an immune response should a receptor associated cancer develop and should be within two days after development of said cancer is noted or determined.

We turn now to the second aspect of the third embodiment.

Anti-VEGFR is described in U.S. Patent Publication 2004-0247597. Dosage is for example 10-5000 μg/kg given IV, e.g., 3 times a week.

The amount of nitric oxide synthesis inhibitor or nitric oxide scavenger for the second aspect of the second embodiment is a VEGFR internalization preventing or inhibiting (dynamin activation preventing or inhibiting) effective amount. Dosage for a particular nitric oxide synthesis inhibitor or nitric oxide scavenger for a particular receptor associated cancer and at risk status can be established by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure or (f) by assessing effect or receptor production. In general, dosage ranges from nanomolar to millimolar blood concentration in vivo. Dosage for LNMA ranges, for example, from 1 μm to 20 mM blood concentration (0.1-20 gms/day) and dosage for vitamin B-12 ranges, for example, from 2-20 mg/day.

The route of administration for nitric oxide synthesis inhibitor or nitric oxide scavenger for the second aspect of the second embodiment can be, for example, oral or IV.

We turn now to the third embodiment herein which is directed to preventing loss of beta agonist responsivity in a heart failure patient with blood pressure of at least 120 mm Hg systolic, (LNMA has previously been administered to raise blood pressure in those with low blood pressure, especially pathologically low blood pressure) or those with blood pressure less than 120 mm Hg systolic without clinical symptoms of shock and with normal peripheral perfusion and tissue oxygenation and without the need for pressor support or who do not have renal dysfunction and/or heart rate greater than 85 (LNMMA has not been previously administered in these cases), and in asthma patients with normal tone (less than 12% decrease in basal FEV1 relative to patient's baseline) (LMA has previously been administered to those with 12% or more decrease in FEV1 relative to the patient's baseline to mitigate inflammation but not to those with normal tone.

We turn firstly to heart failure. In heart failure the beta receptor gets stimulated too much and increased expression of nitric oxide synthase stimulates dynamin activity. This may cause beta agonist desensitization (loss of responsivity), e.g., loss of responsiveness to the beta agonists dobutamine HCI and fenoterol in the treatment of severe congestive heart failure.

The heart failure patients for treatment herein are those having a blood pressure of at least 120 mM Hg systolic or less than 120 mm Hg systolic without clinical symptoms of shock and with normal peripheral perfusion and tissue oxygenation and without the need for pressor support or who do not have renal dysfunction and/or heart rate greater than 85, who are at risk for beta agonist desensitization, e.g., those taking beta agonist or who may be prescribed beta agonists.

The amount of a nitric oxide synthesis inhibitor or nitric oxide scavenger to be administered to the heart failure patient is a beta agonist desensitization preventing amount or a dynamin activation preventing or inhibiting amount. The dosage for a particular nitric oxide synthesis inhibitors or nitric oxide scavenger for a particular heart failure patient can be determined by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure or (f) causes increase in beta agonist responsivity. In general, dosage ranges from nanomolar to millimolar blood concentration in vivo. Dosage for LNMA ranges, for example, from 1 μM to 20 mM blood concentration (0.1-20 g/day) and for vitamin B12 ranges, for example, from 2-20 mg/day.

The route of administration for a heart failure patient is oral or IV.

The duration of administration for a heart failure patient is no more than one month so nitric oxide will be available if needed for an immune response.

The asthma patients for treatment herein are those at risk for desensitization to beta agonists or those who have become desensitized to treatment with beta agonists, e.g., albuterol, epinephrine, or salbutamol. Desensitization is reflected in elevated blood levels of epinephrine and/or breathing symptoms (wheezing, shortness of breath and respiratory distress), and/or worsening of FEV1.

The amount of nitric oxide synthesis inhibitor or nitric oxide scavenger to be administered to an asthma patient is a beta agonist desensitization preventing amount or a dynamin activation preventing or inhibiting amount. The dosage of a particular agent for a particular patient can be determined by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure or (f) causes increase in beta agonist responsivity. In general, dosage ranges from nanomolar to millimolar concentration in blood in vivo. Dosage for LNMA ranges, for example, from 1 µM to 20 mM blood concentration (0.1-20gms/day) and for vitamin B12 ranges, for example, from 2-20 mg/day.

The administration is to an asthma patient with normal tone (less than 12% decrease in basal FEV1) relative to a patient's baseline, to distinguish prior treatment of asthma with nitric oxide synthesis inhibitors or nitric oxide scavengers and to provide a responsive patient when beta agonist therapy is necessary during an acute attack. Administration is not carried out during an asthma attack.

The route of administration is, for example, oral or IV.

Administration to an asthma patient typically is for a week or two, to sensitize receptors and should be of no more than one month duration so nitric oxide will be available if needed for an immune response. It is discontinued if an asthma attack occurs.

We turn now to the fourth embodiment herein which is directed to a spermicidal composition, e.g., spermicidal oil-in-water emulsion or a spermicidal gel or other spermicidal composition comprising a spermicidally effective amount of a spermicide and infection development preventing or mitigating effective amount of a nitric oxide synthesis inhibitor or a nitric oxide scavenger.

The spermicide can be any of those typically used for spermicidal purposes. A preferred spermicide is nonoxynol-9. Other spermicides, include for example, otoxynol-8, benzalkonium chloride and sodium cholate.

The spermicide components are used in a spermicidally effective amount which is well known for those mentioned above. For nonoxynol-9 a spermicidally effective dose ranges, for example, from 20 to 200 mg and typically is present in an amount ranging from 1 to 5% by volume in a spermicidal composition.

The nitric oxide synthesis inhibitor or nitric oxide scavenger is present in an infection development preventing or mitigating effective amount which is a dynamin activation preventing or inhibiting amount. This can be determined for a particular inhibitor or scavenger, for example, by determination of dosage that (a) decreases dynamin enzyme activity in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure or (f) causes increase in beta agonist responsivity. For L-NMA the dosage ranges, for example, from 1 µM to 20 mM, or 1.1 to 20 gms per application. For vitamin B-12, the dose ranges, for example, from 2 to 20 mg/application.

Other components for the spermicidal composition include, for example, glycerol, propylene glycerol, water, gelling agent, e.g., polyquaternium-32 (copolymer of acrylamide and methacryloxyethyl trimethyl ammonium, chloride), preservative, e.g., benzoic acid, benzalkonium chloride, methyl paraben, propyl paraben, and thickening agent.

The spermicidal composition can be, for example, a spermicidal gel or a vaginal cream. These can be applied topically, for example, to a diaphragm or condom.

Said compositions are effective to prevent occurrence or spreading of sexually transmitted diseases and can be used in the normal course and especially in at risk cases.

We turn now to the fifth embodiment herein which is directed to a nasal composition for topical application to nasal mucosa, e.g., in the form of a spray or ointment for the prevention of development infection and/or mitigation of the symptoms thereof.

The nasal steroid component thereof, is a topical nasal steroid, e.g., beclomethasone, triamcinolone, mometasone, budesonide, flunisolide or fluticasone propionate. The nasal steroid is administered in a nasal congestion preventing or mitigating effective amount, e.g., in the amount it is currently administered for this purpose.

The nitric oxide synthesis inhibitor component or nitric oxide scavenger component is present in an infection development preventing or mitigating effective amount which is dynamin activation prevention or inhibiting amount. For any particular nitric oxide synthesis inhibitor or nitric oxide scavenger, the dose can be determined by determining dose that decreases dynamin enzyme activity or assembly in vitro or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure. In general, dosage ranges from nanomolar to millimolar blood concentration in vivo Dosage for LNMA ranges, for example, from 1 µM to 20 mM blood concentration (0.1 to 20 gms/day) and dosage for vitamin B-12 ranges, for example, from 2 to 20 mg/day.

Other components for the nasal composition include, for example, microcrystalline cellulose, sodium carboxymethyl cellulose, benzalkonium chloride, polysorbate 80, phenethyl alcohol, water.

For nasal spray, nasal cream or nasal ointment, the dose for LNMA ranges, for example, from 1 µM to 20 mM per day (1.1 to 20 gm/day) and the dose for vitamin B12 ranges, for example, from 2 to 20 mg per day and it is provided by including in an aliquot for application, e.g., from 0.01 to 0.2% by weight.

The composition application should be discontinued after one month of continuous application and within two days after development of infection to allow nitric oxide presence for immune response.

The nasal compositions herein are readily applied in the form of a spray or cream, in the case of infection at risk cases, e.g., in anticipation or during the course of a flu outbreak or cold pandemic or to premature babies, and to those who are or expected to be immunocompromised.

We turn now to the sixth embodiment herein which is directed to a urinary tract infection prophylaxis composition which is for administration to those at risk for urinary tract infection as described above.

Antimicrobial component is present in a composition for those at risk for microbe caused infection. An antifungal component is present in a composition for those at risk for fungus caused infection.

Antimicrobial components can be, for example, amnoxicillin or a combination of amoxicillin and clavulanate or the combination drug trimethoprin-sulfamethoxazole or quinolones (e.g., ciproflaxin, norfloxacin, ofloxacin or sparfloxacin), or nitrofurantoin.

The antimicrobial component is present in an antimicrobial effective amount which is the amount the antimicrobials are administered now for microbial associated urinary tract infections, e.g., TMP-SMX at 40/200 mg PO daily or thrice weekly or quinoline (50-100 mg/day).

Antifungal components can be, for example, flucytosine or fluconazol.

The antifungal component is present in an antifungal effective amount which is the amount the antifungals are administered now for fungus associated urinary tract infection.

The nitric oxide synthesis component or nitric oxide scavenger component is present in an infection development preventing or infection mitigating effective amount which is a dynamin activation preventing or inhibiting amount. For any particular nitric oxide synthesis inhibitor or nitric oxide scavenger, the dose can be determined by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure. In general, the dose ranges from nanomolar to millimolar concentration in blood. The dose for LNMA ranges from 1 µM to 20 mM (0.1 to 20 gm) per dose and the dose for vitamin B12 ranges, for example, from 2 to 20 mg per dose.

Other components for the urinary tract infection prophylaxis composition include, for example docusate sodium, magnesium stearate, povidone, and sodium starch glycolate.

Administration is normally oral and for no more than one month for reasons set forth above.

We turn now to the seventh embodiment herein which is directed at a composition for EGFR associated cancer in those at risk therefore. EGFR associated cancers and those at risk therefore, are discussed above.

The anti-EGFR antibody can be, for example, Erbitux (cetuximab). The recommended treatment dosage is 400 mg/m$^2$ as in initial loading dose as a 120 minute IV infusion with weekly maintenance dosages of 250 mg/m$^2$ infused over 60 minutes. For the prophylaxis composition herein, the dose should be 10 to 100% of this.

The nitric oxide synthesis inhibitor is included in the infusion in an EGFR blocking effective amount. For any particular nitric oxide synthesis inhibitor, the dosage can be determined by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure. In general, the dosage ranges from nanomolar to millimolar concentration in blood. The dose for LNMA ranges from 1 µM to 20 mM (0.1 to 20 gm) per infusion and the dose for vitamin B12 ranges from 2 to 20 mg per infusion.

The antibody and nitric oxide synthesis inhibitors/nitric oxide scavenger components are preferably administered in phosphate buffered saline.

As indicated above, the composition is for infusion.

Administration of nitric oxide synthesis inhibitor or nitric oxide scavenger is discontinued within two days after development of cancer is noted or determined, for reasons set forth above.

We turn now to the eighth embodiment herein which is directed to a human blood component(s) composition (e.g., comprising whole blood, red blood cells, plasma, hemoglobin based blood substitutes, albumin, platelets, or white blood cells) for infusion.

The nitric oxide synthesis inhibitor or nitric oxide scavenger is present as an additive in an infection development preventing or infection mitigating amount. For any particular nitric oxide synthesis inhibitor or nitric oxide scavenger, the amount can be determined by determining dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure. In general, the amount ranges from nanomolar to millimolar concentration of blood components. For LNMA the amount range is, for example, from 0.5 to 5 g/unit. For vitamin B-12, this amount ranges from 2 to 20 g/unit of blood components.

The composition can contain the usual preservative additives.

I turn now to the ninth embodiment herein which is directed to a method of treating a mammal affected with a disorder treated by receptor blocking therapy comprising administering a receptor blocking effective amount of receptor blocker and a said receptor internalization preventing or inhibiting (or a dynamin activation preventing or inhibiting) effective amount of a nitric oxide synthesis inhibitor or a nitric oxide scavenger. The nitric oxide synthesis inhibitor and nitric oxide scavenger administration keeps the receptors or the cell surfaces where they are good targets for the blockers.

The term "receptor blocking therapy" includes antibodies to the receptors as well as non antibody blockers of the receptors.

Antibody receptor blockers and the diseases they are administered to ameliorate include, for example, rituximab including Rituxan® and Zevalin® (B-cell lymphomas including non-Hodgkin lymphomas), tositumomab (B-cell lymphomas), trastuzumab (breast cancers associated with overexpression of HER-2/neu), cetuximab (colorectal cancer), gemtuzimab oxogmycin (conjugated monoclonal antibody ) (acute myelogenous leukemia, AML), alemtuzumab (chronic lymphocytic leukemia, CLL) bevacizumab (colorectal cancer), abciximab (restenosis), anti-VEGFR (atherosclerosis).

Non antibody receptor blockers and the disorders they are administered to ameliorate include, for example, carteolol hydrochloride and metapranolol (high intraocular pressure).

The receptor blockers can be administered in the ninth embodiment herein in the same amounts and by the same routes of administration as they are now administered without nitric oxide synthesis or nitric oxide scavenger administration.

The nitric oxide synthesis inhibitor or nitric oxide scavenger for the ninth embodiment herein is administered in an amount effective to maintain receptors that are being blocked, on cell surface (i.e., a dynamin activation preventing or inhibiting effective amount).

Dosage for the ninth embodiment for a particular nitric oxide synthesis inhibitor or nitric oxide scavenger can be established by determination of dosage that (a) decreases dynamin enzyme activity or assembly in vitro, or (b) causes decrease in nitric oxide metabolites in blood in vivo, or (c) causes decrease in nitric oxide bound hemoglobin in vivo or (d) causes decrease in expired nitric oxide in vivo or (e) causes slight (e.g., 5 mm Hg) increase in blood pressure or (f) by assessing effect or receptor production. In general, dosage ranges from nanomolar to millimolar blood concentration in vivo. Dosage for LNMA ranges, for example, from 1 µM to 20 mM blood concentration (0.1 to 20 gms/day) and dosage for vitamin B-12 ranges, for example, from 2 to 20 mg/day.

Administration of nitric oxide synthesis inhibitor or nitric oxide scavenger is, for example, IV or oral, and is preferably administered together with receptor blocker.

Elements of the invention and background thereof is described in Wang, G., et al., PNAS 103(5), 1295-1300, published on-line Jan. 23, 2006 and titled "Nitric Oxide Regulates Endocytosis by S-nitrosylation of Dynamin" (hereinafter Wang, et al.).

The invention is explained and illustrated by the following Background Examples and Working Examples.

BACKGROUND EXAMPLE 1

This is set forth in Wang, et al. which shows that nitric oxide regulates endocytosis by S-nitrosylation of dynamin at a single system residue (C607) and that a mutant protein bearing a C607A substitution does not increase its endocytotic activity in response to nitric oxide and that the expression of dynamin C607A inhibits both receptor internalization and bacterial invasion. FIG. 2 of Wang, et al. shows the S-nitrosylation; FIG. 1 of Wang, et al. demonstrates that nitric oxide synthesis inhibitor which blocks the S-nitrosylation, blocks internalization.

BACKGROUND EXAMPLE 2

HIV infection assay was carried out as follows: 293T cells were co-transfected with two plasmids one encoding the envelope proteins (from HIV (denoted NL4-3), AMLV, or VSV) and the other encoding a modified HIV genome—the nef gene of HIV was replaced by a luciferase gene, and the envelope gene of HIV was deleted), The supernatants from these cells (virions) were collected and virus titer was standardized on U87 cells and used to infect the T cells. Anti-CD4 (an HIV receptor (CD4) antibody) or inhibitor was added to T cells at the time of virus infection and the mixture was incubated for 40 hours. Inhibitor A is the nitric oxide synthesis inhibitor L-NAME. Compound C is an inhibitor of c-Src-tyrosine kinase. Inhibitor D targets protein kinase C. The inhibitor alone does not affect viral/cellular viability. The virus titer used was $10^5$ to $10^6$, and virus internalization was determined using a luciferase assay.

Data obtained is shown in Table 1 below where the middle column indicates cells infected and the right column indicates the percent infected compared to envelope protein with no anti-CD4 or inhibitor.

TABLE 1

|  | Mean | % Infection |
|---|---|---|
| Cells Only | 66 |  |
| NL4-3 | 108400 |  |
| Anti-CD4 | 171 | 0.2% |
| Inhibitor A | 50359 | 46.5% |
| Compound C | 132182 | 121.9% |
| Inhibitor D | 60144 | 55.5% |
| AMLV | 164904 |  |
| Anti-CD4 | 157357 | 95.4% |
| Inhibitor A | 60090 | 36.4% |
| Compound C | 202645 | 122.9% |
| Inhibitor D | 117507 | 71.3% |
| VSV |  |  |
| Anti-CD4 | 163230 | 56.9% |
| Inhibitor A | 120209 | 41.9% |
| Compound C | 320369 | 111.7% |
| Inhibitor D | 196281 | 68.4% |

WORKING EXAMPLE I

A 28-year-old white female finds that her partner the previous night is HIV positive. She presents to the Emergency Room where she is given a prophylactic dose of AZT (600 mg dose) and a dose of 1 gm L-NMMA Q 6 hrs for 3 days. Blood titers for HIV are restive at day 7.

WORKING EXAMPLE II

A patient is exposed to blood infected by "E.coli" and HIV following coronary artery bypass surgery. AZT (prophylactic dose of 600 mg) and B12 (which scavenges NO) (dose 10 mg) are given in combination with ampicillin (prophylactic dose of 1 gm) for 6 days Bacterial and HIV titer are undetectable at a week.

WORKING EXAMPLE III

An immunocompromised patient at risk for colon cancer is given an initial loading dose of 200 mg/$M^2$ cetuximab as a 120 minute infusion with weekly maintenance doses of 125 mg/$M^2$ over 60 minutes weekly. Perfusion rate is 4 mL/min. Concurrently the patient is infused with 5 gm LNMA or 10 mg vitamin B12. Two years later the patient is colon cancer free.

WORKING EXAMPLE IV

A 60 year old with heart failure is admitted to a hospital for a dobutamine holiday (where a congestive heart failure patient spends 1-2 days in the hospital to receive a dobutamine drip every month or so). The patient is administered 0.1 mg/kg LNMA for 24 hours. Beta agonist sensitive response as measured by cardiac output improves from 3 L/min. to 3.5 L/min.

WORKING EXAMPLE V

A 30-year old asymptomatic Hispanic female who normally has four exacerbations of asthma per year is given 1 gm/day LNMA four times a week for a year. Exacerbation frequency decreases to once a year.

WORKING EXAMPLE VI

Sperimcidal Composition for Application to a Vaginal Sponge.

|  | wt % | mg |
|---|---|---|
| Nonoxynol-9 | 10 | 165 |
| Vitamin B-12 | 0.6 | 10 |
| Pectin | 0.5 | 8.25 |
| Povidone-Iodine | 0.16 | 2.64 |
| Sodium carboxy methylcellulose | 0.125 | 2.068 |
| Methyl puraben | 0.050 | 0.825 |
| Lactic Acid | 0.050 | 0.825 |
| Sodium benzoate | 0.1 | 1.65 |
| Distilled water | 88.07 | 1453.138 |
|  | 100% | 1650 mg |

The user of the sponge found her partner to be hepatitis C infected. The user did not become hepatitis C infected.

WORKING EXAMPLE VII

Nasal Spray.

| | |
|---|---|
| Oxymetazoline hydrochloride (decongestant) | 2.5 g |
| Beclomethasone dipropionate (corticosteroid) | 2.5 g |
| L-NMA | 5 g |
| Hydroxymethyl cellulose | 5 g |
| Sodium edentate | 2.5 g |
| Benzalkonium chloride | 0.625 g |
| Sorbitol solution 70% | 333.3 g |
| Purified water | To 5 liters |

The composition is administered once or twice daily, one or two metered doses of 140 mg to each nostril to school children during a cold outbreak. The treated children do not develop a cold.

WORKING EXAMPLE VIII

Urinary Tract Infection Prophylaxis Composition.
Tablet Containing:

| | |
|---|---|
| Trimethoprin | 80 mg |
| Sulfamethoxazole | 400 mg |
| Vitamin B-12 | 20 mg or LNMA 2 gm |
| Docusate sodium | 0.4 mg |
| Magnesium stearate | 1.0 |
| Povidone | 3.5 |
| Sodium starch glycolate | 10.0 |

A 20 year old female with frequent urinary tract infections is given 1 tablet the day after intercourse. Urinary tract infection does not occur.

WORKING EXAMPLE IX

Composition For Prophylaxis of EGFR Associated Cancer.
For each 50 ml vial:
100 mg cetuximab
at a concentration of 2 mg/ml
1mg LNMA or 2 mg Vitamin B-12
8.48 mg/ml sodium chloride
1.88 mg/ml sodium phosphate dibasic heptahydrate
0.42 mg/ml sodium phosphate monohydrate
water for injection to 50 mg
The composition is administered in the case of Working Example III.

WORKING EXAMPLE X

In the above examples where LNMA is administered L-NAME is administered at a dosage ranging from 10 to 1000 mg/kg.

WORKING EXAMPLE XI

Whole blood containing 1 gm L-NMA per unit is transfused into a patient. It is later found that the blood is infected with hepatitis C. The patient does not develop hepatitis C.

WORKING EXAMPLE XII

A 60-year old male with atherosclerosis is administered 100 mg/kg anti-VEGFR three times a week via infusion and 2 gms/day of L-NMA or 10 mg/day vitamin B-12. Six months later plaque is not destabilized and no heart attack has occurred.

WORKING EXAMPLE XIII

A 30-year old with EGFR expressing metastatic colorectal cancer is given an initial loading dose of 400 mg/m$^2$ cebuximab as a 120 minute infusion at 2.5 mL/min with weekly maintenance doses of 250 mg/M$^2$ over 60 minutes at 2.5 mL/min. Concurrently the patient is infused with 5 gm L-NMA or 10 mg vitamin B12. Improvement in disease related symptoms is noted.

WORKING EXAMPLE XIV

A 65 year old patient with unstable angina presents to the emergency room.
Abciximab is administered at 0.25 mg/kg as an intravenous bolus followed by infusion of 0.125 mg/kg/min for 12 hours. Heparin is concurrently administered in a different line with an initial dosage of 70 μg/kg with continuing infusion to maintain ACT of 200-300.
L-NMA (5g) or 10 mg vitamin B-12 is administered IV through a different line.
Need for urgent revascularization is only 2% at 30 days.

WORKING EXAMPLE XV

A 45 year old man (patient) is exposed to a subject who tests positive for bird flu. The patient is started on minocycline (a nitric oxide synthesis inhibitor), 500 mg p.o. t.i.d. for one week. The patient develops a fever and malaise and is started on Tamiflu® (oseltamivir phosphate), 75 mg, p.o. b.i.d. After one additional week, minocycline is stopped. Tamiflu® is continued for seven days. The patient does not develop respiratory distress and improves.

WORKING EXAMPLE XVI

After a classmate tests positive for the flu, a nine year old child is given tetracycline, 30 mg/kg daily in 3 divided portions (a nitric oxide synthase inhibitor). Four days later flu symptoms appear. Tetracycline is discontinued and Tamiflu®, 75 mg, p.o., b.i.d. is given for 5 days. The patient is mildly sick for 1 day and then goes back to school.

WORKING EXAMPLE XVII

An immunocompromised patient is exposed to a patient diagnosed with influenza. The patient is given 5 gms/day L-NMA p.o. After one week the patient tests positive for influenza A and L-NMA administration is stopped and the patient is given amantadine, 100 mg p.o., b.i.d. for two weeks. Flu symptoms disappear.

Variations

The foregoing description of the invention has been presented describing certain operable and preferred embodiments. It is not intended that the invention should be so limited since variations and modifications thereof will be obvious to the skilled in the art, all of which are within the spirit and scope of the invention.

What is claimed is:

1. A method of prophylaxis against bacterial and/or viral infection in a mammal at risk for a bacterial or a viral infection, said method comprising administering to said mammal an infection development preventing or mitigating effective amount (or a dynamin activation preventing or inhibiting effective amount) of a nitric oxide synthesis inhibitor or a nitric oxide scavenger and discontinuing said administration within one month or within two days after infection is observed or determined in the mammal, whichever is shorter.

2. The method of claim 1, where the mammal is at risk for development of bird flu infection and an infection preventing or mitigating amount of antibiotic nitric oxide synthesis inhibitor is what is administered.

3. The method of claim 2 where the antibiotic nitric oxide synthesis inhibitor administered is minocycline.

4. A method of prophylaxis of development in a mammal at risk for development of a cancer where overstimulation of a receptor, contributes to development of the cancer, comprising administering to said mammal a said receptor internalization inhibiting amount of a nitric oxide synthesis inhibitor or a nitric oxide scavenger and discontinuing administration within a month or within two days after said cancer is observed or determined in the mammal, whichever is shorter.

5. A method of preventing loss of beta agonist responsivity in a heart failure patient with compensated heart failure or in asthma patient with normal tone comprising administering to the heart failure patient or administering to the asthma patient between exacerbations a beta agonist desensitization preventing amount of a nitric oxide synthesis inhibitor or nitric oxide scavenger.

6. A method of prophylaxis against heart attack in a mammal with plaque accumulation, comprising administering an amount of anti-vascular endothelial growth factor receptor antibody effective to prevent destabilization of plaque and a vascular endothelial growth factor receptor internalization preventing or inhibiting effective amount of a nitric oxide synthesis inhibitor or a nitric oxide scavenger, and discontinuing administration of the nitric oxide synthesis inhibitor or nitric oxide scavenger within a month or if a heart attack occurs.

7. A spermicidal composition gel comprising a spermicidally effective amount of a spermicide and an infection preventing or inhibiting effective amount of an nitric oxide synthesis inhibitor or an nitric oxide scavenger.

8. A nasal composition for topical application for the prevention of development of infection and/or mitigation of the symptoms thereof, comprising a nasal congestion preventing or mitigating effective amount of a nasal steroid and an infection preventing or mitigating effective amount of an NO synthesis inhibitor or an NO scavenger.

9. A urinary tract infection prophylaxis composition comprising an infection preventing or infection mitigating effective amount of a non- antibiotic NO synthesis inhibitor or an NO scavenger and an antimicrobial effective of an antimicrobial and/or an antifungal effective amount of an antifungal.

10. A composition comprising an anti-EGER blocking effective amount of anti-EGER antibody and an EGFR blocking effective amount of an NO synthesis inhibitor or an NO scavenger.

11. Human blood component(s) composition for transfusion into a human in need thereof comprising whole blood, red blood cells, plasma, hemoglobin based blood substitute, albumin, platelets and/or white blood cells, and a dynamin blocking effective amount of an NO synthesis inhibitor or an NO scavenger.

12. A method for treating a mammal affected with a disorder treated by receptor blocking therapy comprising administering a receptor blocking effective amount of a receptor blocker and a receptor internalization preventing or inhibiting effective amount of a nitric oxide synthesis inhibitor or a nitric oxide scavenger so that receptors remain on cell surface to be exposed to the receptor blocking therapy.

13. A method for treating a mammal at risk for and later developing flu or bird flu, comprising administering to the mammal in accordance with the method of claim 1 and when infection develops administering an antiviral effective amount of oseltamivir phosphate.

14. The method of claim 4 where the receptor is EGFR.

* * * * *

UNITED STATES PATENT AND TRADEMARK OFFICE
CERTIFICATE OF CORRECTION

| | |
|---|---|
| PATENT NO. | : 7,531,164 B2 |
| APPLICATION NO. | : 11/544559 |
| DATED | : May 13, 2009 |
| INVENTOR(S) | : Yehia Daaka and Jonathan S. Stamler |

It is certified that error appears in the above-identified patent and that said Letters Patent is hereby corrected as shown below:

Claim 10 (column 18, line 14), change "EGER" to --EGFR--.

Claim 10 (column 18, line 15), change "EGER" to --EGFR--.

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,531,164 B2  Page 1 of 1
APPLICATION NO. : 11/544559
DATED : May 12, 2009
INVENTOR(S) : Yehia Daaka and Jonathan S. Stamler It is certified that error appears in the above-identified patent and that said Letters Patent is hereby corrected as shown below:

Claim 10 (column 18, line 14), change "EGER" to --EGFR--.

Claim 10 (column 18, line 15), change "EGER" to --EGFR--.

This certificate supersedes the Certificate of Correction issued June 9, 2009.

Signed and Sealed this

Seventh Day of July, 2009

JOHN DOLL
*Acting Director of the United States Patent and Trademark Office*